United States Patent
Thomas et al.

(10) Patent No.: US 6,645,727 B2
(45) Date of Patent: Nov. 11, 2003

(54) ANTIBODY COMPOSITIONS FOR PREPARING ENRICHED MESENCHYMAL PROGENITOR PREPARATIONS

(75) Inventors: Terry Thomas, Vancouver (CA); Emer Clarke, Vancouver (CA)

(73) Assignee: StemCell Technologies Inc., Vancouver (CA)

( * ) Notice: Subject to any disclaimer, the term of this patent is extended or adjusted under 35 U.S.C. 154(b) by 67 days.

(21) Appl. No.: 09/864,884

(22) Filed: May 25, 2001

(65) Prior Publication Data

US 2002/0058289 A1 May 16, 2002

Related U.S. Application Data

(60) Provisional application No. 60/207,368, filed on May 26, 2000.

(51) Int. Cl.[7] ................ G01N 33/567; C12N 5/00; C12N 5/02; C12N 5/08; C07K 16/00
(52) U.S. Cl. ................ 435/7.21; 435/325; 435/366; 530/387.1
(58) Field of Search ................ 435/7.21, 325, 435/366; 530/387.1

(56) References Cited

U.S. PATENT DOCUMENTS

| | | |
|---|---|---|
| 5,486,359 A | 1/1996 | Caplan et al. |
| 5,643,736 A | 7/1997 | Bruder et al. |
| 5,733,542 A | 3/1998 | Haynesworth et al. |

OTHER PUBLICATIONS

Allay, J.A. et al., *Human Gene Therapy*. 8:1417–1427 (1997).
Bruder, S.P. et al., *J. Cell. Biochem*.. 64:278–294 (1997).
Majumdar, M.K. et al., *J. Cell. Physiol*. 176:57–66 (1998).
Pittenger, M.F., et al. *Science*. 284:143–147 (1999).
Reyes, M. et al. *Blood* 92:725a (1998).

*Primary Examiner*—Christina Chan
*Assistant Examiner*—M. Belyavskyi
(74) *Attorney, Agent, or Firm*—Bereskin & Parr; Micheline Gravelle

(57) ABSTRACT

The present invention relates to antibody composition that are useful in preparing enriched mesenchymal progenitor cell preparations. The invention also relates to kits for carrying out the processes and to the cell preparations prepared by the processes.

18 Claims, 2 Drawing Sheets

ANTIBODY COMPOSITIONS FOR PREPARING ENRICHED MESENCHYMAL PROGENITOR PREPARATIONS

This application claims the benefit under 35 USC §119(e) of U.S. provisional application No. 60/207,368 filed May 26, 2000.

FIELD OF THE INVENTION

The present invention relates to novel antibody compositions, and processes and kits for preparing cell preparations enriched for mesenchymal progenitors.

BACKGROUND OF THE INVENTION

The bone marrow microenvironment regulates both positively and negatively, the proliferation, maturation and differentiation of hematopoietic stem cells (1). The microenvironment is made up of "stromal cells" which are believed to be derived from a pluripotent cell in the marrow. The stromal cell precursor, detected as a colony forming unit fibroblast (CFU-F), is distinct from other hematopoietic stem cells (2). In addition to supporting hematopoietic cells, stromal cells can differentiate into bone, cartilage, muscle and tendon (3, 4) and for these reasons the term mesenchymal stem cell (MSC) has been adopted. Although the CFU-F assay has been used in vitro to correlate with mesenchymal cell potential (5), the relationship between the cells capable of producing CFU-F and MSC has not yet been fully established. The CFU-F assay has been used to evaluate the bone marrow microenvironment in normal donors (6), in diseased states (7, 8) and following chemotherapy (9). There is much clinical interest in these cells and the following clinical applications are being evaluated:

expansion and reinfusion of MSC into patients in an attempt to reconstitute the microenvironment and provide optimal conditions to support hematopoiesis (10)

gene transfer into MSC (11)

repair of mesenchymal tissues (12, 13)

U.S. Pat. No. 5,643,736 describes markers on mesenchymal cells and a positive selection (method for isolating the cells). Negative selection of mesenchymal progenitors has used anti-CD45 alone or in combination with anti-glycophorin A (Verfaillie et al. 1998). However, the inventors have found that Immunoadsorption with anti-CD45 depletes mesenchymal precursors present in bone marrow as assayed in the CFU-F (colony forming unit fibroblast) functional assay.

In view of the foregoing, there is a need in the art to develop novel methods to prepare cell preparations enriched for mesenchymal progenitors.

SUMMARY OF THE INVENTION

The inventors have developed antibody compositions for use in preparing cell preparations highly enriched for mesenchymal progenitor cells in a negative selection protocol. The antibodies in the antibody composition are specific for selected markers associated with cells that are other than mesenchymal progenitor cells thereby allowing them to be removed from the cell preparation. In particular, the present inventors have found that an antibody composition containing antibodies specific for the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig gives a cell preparation highly enriched for mesenchymal progenitor cells. This antibody composition may be generally referred to herein as the mesenchymal progenitor enrichment composition or cocktail. Optionally, the mesenchymal progenitor enrichment composition additionally includes antibodies to CD14, CD33, CD34, CD38, CD56, IgE or glycophorin A.

In a preferred embodiment, the mesenchymal progenitor enrichment composition comprises antibodies specific for the antigens (a)CD2 and/or CD3 and/or CD5 and/or both CD4 and CD8; (b) CD66b and/or CD16 and/or CD11b and/or CD15; (c) CD19 and/or CD20 and/or CD21 and/or CD22 and/or CD24 and/or Ig; (d) CD14; and (e) CD33 and/or CD38.

The enrichment and recovery of mesenchymal progenitor cells using the antibody compositions of the invention in a negative selection technique has many advantages over conventional positive selection techniques. Highly enriched cell preparations can be obtained using a single step. The cells obtained using the antibody composition of the invention are not labeled or coated with antibodies or modified making them highly suitable for many uses.

The present invention also relates to a negative selection process for enriching and recovering mesenchymal progenitor cells in a sample comprising: (1) reacting the sample with an antibody composition containing antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig under conditions permitting the formation of conjugates between the antibodies and cells in the sample having the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig on their surfaces; (2) removing the conjugates; and (3) recovering a cell preparation which is enriched in mesenchymal progenitor cells.

In a specific embodiment, the mesenchymal progenitor enrichment composition may be used in an immunorosetting method wherein the cells to be depleted are rosetted with red blood cells or erythrocytes. In such an embodiment, each of the antibodies in the mesenchymal progenitor enrichment composition is linked to an antibody that binds to erythrocytes.

Accordingly, the present invention provides a negative selection immunorosetting method for enriching and recovering mesenchymal progenitor cells in a sample containing the mesenchymal progenitor cells, erythrocytes and undesired cells comprising: (1) contacting the sample with an antibody composition comprising (i) antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig linked to (ii) at least one antibody that binds to the erythrocytes, under conditions to allow immunorosettes of the undesired cells and the erythrocytes to form; and (2) separating the immunorosettes from the remainder of the sample to obtain a sample enriched in mesenchymal progenitor cells.

The present invention also relates to a kit useful in preparing a cell preparation enriched in mesenchymal progenitor cells comprising antibodies specific for the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig, and instructions for preparing a cell preparation enriched in mesenchymal progenitor cells.

The invention further relates to cell preparations obtained in accordance with the processes of the invention. The invention still further contemplates a method of using the antibody compositions of the invention in negative selection methods to recover a cell preparation which is enriched in mesenchymal progenitor cells.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described with reference to the accompanying drawings, in which.

DETAILED DESCRIPTION OF THE INVENTION

I. Antibody Compositions

Figure 1:
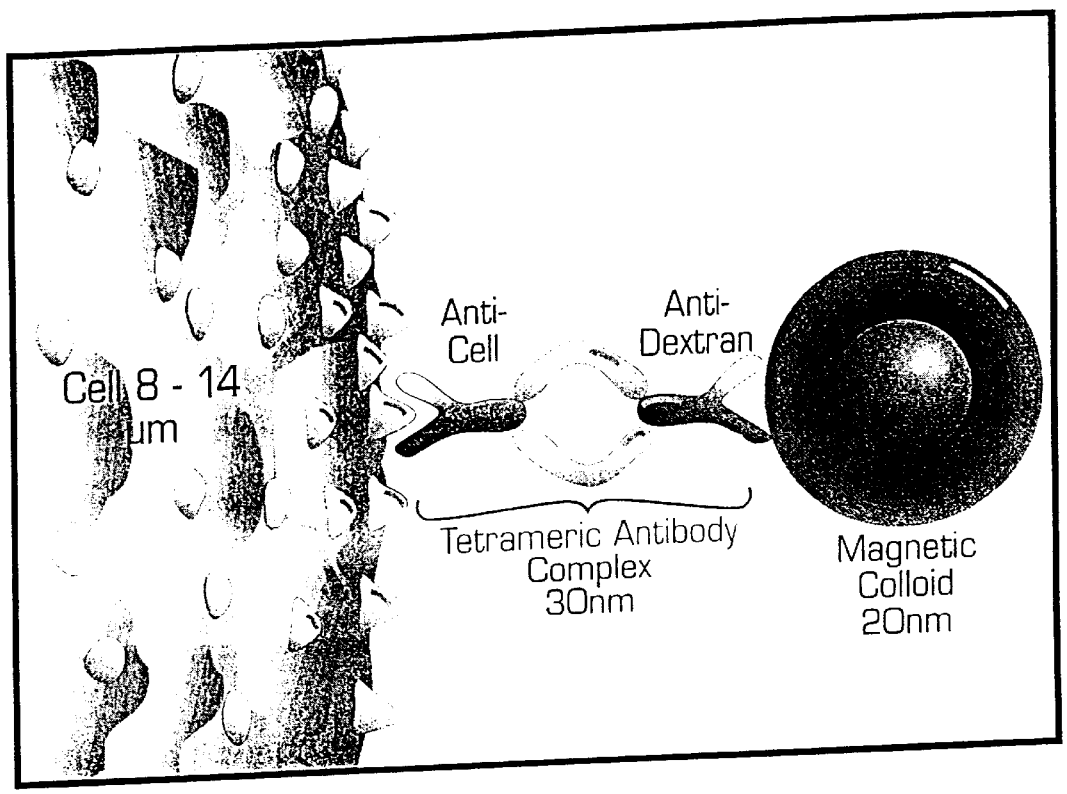
FIG. 1 is a schematic representation of magnetic cell labeling using tetrameric antibody complexes and colloidal dextran iron.

As hereinbefore mentioned, the invention relates to an antibody compositions for preparing cell preparations enriched in mesenchymal progenitor cells. In one aspect, the antibody composition comprises antibodies specific for the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig, which are present on the surface of non-mesenchymal progenitor cells. Preferably, the antibody composition comprises antibodies specific for the antigens CD3, CD66b and CD19.

The above antibody composition may additionally include other antibodies such antibodies that can bind to the antigens CD14, CD33, CD34, CD38, CD56, IgE or glycophorin A.

In one preferred embodiment, the antibody composition comprises antibodies specific for the antigens (a) CD2 and/or CD3 and/or CD5 and/or both CD4 and CD8; (b) CD66b and/or CD16 and/or CD11b and/or CD15; (c) CD19 and/or CD20 and/or CD21 and/or CD22 and/or CD24 and/or Ig; (d) CD14; and (e) CD33 and/or CD38. In a specific embodiment, the antibody composition comprises antibodies specific for the antigens (a) CD3; (b) CD66b; (c) CD19; (d) CD14 and (e) CD33 or CD38, more preferably (a) CD3; (b) CD66b; (c) CD19; (d) CD14 and (e) CD38.

In another preferred embodiment, the antibody composition comprises antibodies specific for the antigens (a) CD2 and/or CD3 and/or CD5 and/or both CD4 and CD8; (b) CD66b and/or CD16 and/or CD11b and/or CD15; (c) CD19 and/or CD20 and/or CD21 and/or CD22 and/or CD24 and/or Ig; (d) CD14; (e) CD33 and/or CD38; and (f) CD56.

One skilled in the art will appreciate that in addition to the antibodies listed above, the mesenchymal progenitor cells enrichment cocktail may additionally include other antibodies that are specific for antigens on the surface of non-mesenchymal progenitor cells. The selection of the antibodies can depend on many factors including the nature of the sample to be enriched. Antibodies useful in the invention may be prepared as described below using techniques known in the art or may be obtained from commercial sources.

Within the context of the present invention, antibodies are understood to include monoclonal antibodies and polyclonal antibodies, antibody fragments (e.g., Fab, and F(ab')$_2$) and chimeric antibodies. Antibodies are understood to be reactive against a selected antigen on the surface of a cell if they bind with an appropriate affinity (association constant), e.g. greater than or equal to $10^7$ M$^{-1}$.

Polyclonal antibodies against selected antigens on the surface of cells may be readily generated by one of ordinary skill in the art from a variety of warm-blooded animals such as horses, cows, various fowl, rabbits, mice, hamsters, or rats. For example, a mammal, (e.g., a mouse, hamster, or rabbit) can be immunized with an immunogenic form of an antigen which elicits an antibody response in the mammal. Techniques for conferring immunogenicity on an antigen include conjugation to carriers or other techniques well known in the art. For example, the antigen can be administered in the presence of adjuvant. The progress of immunization can be monitored by detection of antibody titers in plasma or serum. Following immunization, antisera can be obtained and polyclonal antibodies isolated from the sera.

Monoclonal antibodies are preferably used in the antibody compositions of the invention. Monoclonal antibodies specific for selected antigens on the surface of non-mesenchymal progenitor cells may be readily generated using conventional techniques. For example, monoclonal antibodies may be produced by the hybridoma technique originally developed by Kohler and Milstein 1975 (Nature 256, 495–497; see also U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKeam, and Bechtol (eds.), 1980, and Antibodies: A Laboratory Manual, Harlow and Lane (eds.), Cold Spring Harbor Laboratory Press, 1988). Other techniques may also be utilized to construct monoclonal antibodies (for example, see William D. Huse et al., 1989, "Generation of a Large Combinational Library of the Immunoglobulin Repertoire in Phage Lambda," Science 246:1275–1281, L. Sastry et al., 1989 "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732; Kozbor et al., 1983 Immunol. Today 4, 72 re the human B-cell hybridoma technique; Cole et al. 1985 Monoclonal Antibodies in Cancer Therapy, Allen R. Bliss, Inc., pages 77–96 re the EBV-hybridoma technique to produce human monoclonal antibodies; and see also Michelle Alting-Mees et al., 1990 "Monoclonal Antibody Expression Libraries: A Rapid Alternative to Hybridomas," Strategies in Molecular Biology 3:1–9). Hybridoma cells can be screened immunochemically for production of antibodies specifically reactive with an antigen, and monoclonal antibodies can be isolated.

The term "antibody" as used herein is intended to include antibody fragments which are specifically reactive with specific antigens on the surface of non-mesenchymal progenitor cells. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

The invention also contemplates chimeric antibody derivatives, i.e., antibody molecules that combine a non-human animal variable region and a human constant region.

Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Antibodies may be selected for use in the antibody compositions of the invention based on their ability to deplete targeted non-mesenchymal progenitor cells and recover non-targeted cells (i.e. mesenchymal progenitor cells) in magnetic cell separations as more particularly described herein, and in U.S. Pat. No. 5,514,340, which is incorporated in its entirety herein by reference.

In a specific embodiment, the mesenchymal progenitor enrichment composition may be used in an immunorosetting method wherein the nucleated cells to be depleted are rosetted with red blood cells or erythrocytes. In such an embodiment, each of the antibodies in the mesenchymal progenitor enrichment composition are linked to an antibody that binds to erythrocytes. The two antibodies (a) and (b) may be directly linked by preparing bifunctional or bispecific antibodies. The two antibodies (a) and (b) may be indirectly linked for example, by preparing tetrameric antibody complexes. All of these are described hereinafter.

In one aspect, the antibody specific for the nucleated cells is linked directly to the antibody specific for the erythrocytes. In one embodiment, the antibody composition of the present invention contains bifunctional antibodies wherein each antibody in the mesenchymal progenitor enrichment composition is linked directly to (b) at least one antibody specific for the erythrocytes. Bifunctional antibodies may be prepared by chemically coupling one antibody to the other, for example by using N-succinimidyl-3-(2-pyridyldithio) propionate (SPDP).

In another embodiment, the antibody composition contains bispecific antibodies. Bispecific antibodies contain a variable region of an antibody specific for erythrocytes and a variable region of an antibody in the mesenchymal progenitor enrichment composition. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

In another aspect, the antibody composition of the present invention comprises (a) each antibody in the mesenchymal progenitor enrichment composition indirectly linked to (b) at least one antibody specific for the erythrocyte. By "indirectly linked" it is meant that antibody (a) and antibody (b) are not directly covalently linked to each other but are attached through a linking moiety such as an immunological complex. In a preferred embodiment, the antibody in the mesenchymal progenitor enrichment composition is indirectly linked to the antibody specific for the erythrocytes by preparing a tetrameric antibody complex. A tetrameric antibody complex may be prepared by mixing a first monoclonal antibody which is capable of binding to the erythrocytes, and a second monoclonal antibody capable of binding the nucleated cells to be separated. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the $F(ab')_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

Preferably, the antibody specific for the erythrocytes is anti-glycophorin A. The anti-glycophorin A antibodies contained in the antibody composition of the invention are used to bind the erythrocytes. Examples of monoclonal antibodies specific for glycophorin A are 2B7.1 (StemCell Technologies), 10F7MN (U.S. Pat. No. 4,752,582, Cell lines: ATCC accession numbers HB-8162), and D2.10 (Immunotech, Marseille, France).

Figure 2:
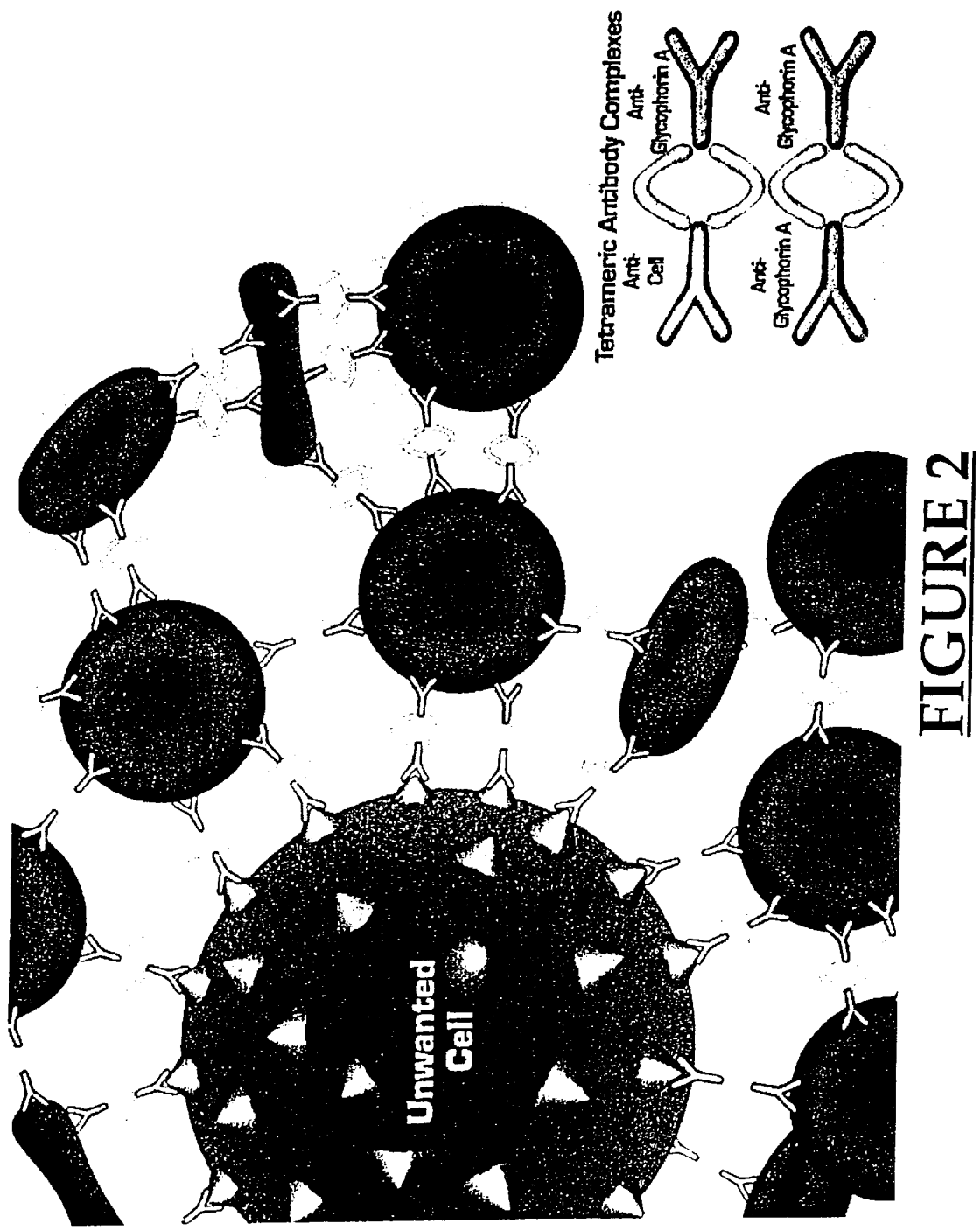
FIG. 2 is a schematic diagram of a rosette of erythrocytes formed around an unwanted nucleated cell using tetrameric antibody complexes.

In a preferred embodiment, the antibody composition is a tetrameric complex comprising (a) anti-glycophorin A antibodies to bind the erythrocytes, (b) an antibody that binds to a nucleated cell type that one wishes to immunorosette and (c) antibodies that bind the Fc portion of both (a) and (b), optionally $F(ab')_2$ antibody fragments. The molar ratio of (a):(b):(c) may be approximately 1:3:4. When several types of cells are to be separated, complexes are made with several anti-nucleated cell antibodies (b). The complexes may then be mixed together to form an antibody composition for use in the method of the invention. FIG. 2 is a schematic diagram of a rosette formed by tetrameric antibody complexes.

II. Process for Preparing Enriched Mesenchymal Progenitor Cell Preparations

The antibody compositions of the invention may be used to enrich and recover mesenchymal progenitor cell preparations. The mesenchymal progenitor cells may be enriched from many samples including bone marrow and peripheral blood.

In accordance with a process of the invention, the sample is reacted with an antibody composition containing antibodies which are specific for selected antigens on the surface of the non-mesenchymal progenitor cells to be removed from the sample and not on the mesenchymal progenitor cells to be enriched in the sample, under suitable conditions, conjugates form between the antibodies contained in the antibody composition and the cells in the sample containing the antigens on their surface; and the conjugates are removed to provide a cell preparation enriched in mesenchymal progenitor cells.

In one aspect the present invention provides a negative selection process for enriching and recovering mesenchymal progenitor cells in a sample comprising (1) reacting the sample with an antibody composition containing antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig, under conditions so that conjugates are formed between the antibodies and cells in the sample containing the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig on their surfaces; (2) removing the conjugates; and, (3) recovering a cell preparation which is enriched in mesenchymal progenitor cells. Other antibody compositions that may be used in the process of the invention include the antibody compositions described above under I. Antibody Compositions as well as the specific compositions described in the Examples.

In the above negative selection processes of the invention for mesenchymal progenitor cell enrichment, conditions which permit the formation of conjugates may be selected having regard to factors such as the nature and amounts of the antibodies in the antibody composition, and the estimated concentration of targeted cells in the sample.

The antibodies in the antibody compositions may be labelled with a marker or they may be conjugated to a matrix. Examples of markers are biotin, which can be removed by avidin bound to a support, and fluorochromes, e.g. fluorescein, which provide for separation using fluorescence activated sorters. Examples of matrices are magnetic beads, which allow for direct magnetic separation (Kernshead 1992), panning surfaces e.g. plates, (Lebkowski, J. S, et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), dense particles alone (Zwerner et al., Immunol. Meth. 1996 198 (2):199–202) adsorption columns (Berenson et al. 1986, Journal of Immunological Methods 91:11–19.), and adsorption membranes. The antibodies may also be joined to a cytotoxic agent such as complement or a cytotoxin, to lyse or kill the targeted cells.

The antibodies in the antibody compositions may be directly or indirectly coupled to a matrix. For example, the antibodies in the compositions of the invention may be chemically bound to the surface of magnetic particles for example, using cyanogen bromide. When the magnetic particles are reacted with a sample, conjugates will form between the magnetic particles with bound antibodies specific for antigens on the surfaces of the non-mesenchymal progenitor cells, and the non-mesenchymal progenitor cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody compositions may also be incorporated in antibody reagents which indirectly conjugate to a matrix. Examples of antibody reagents are bispecific antibodies, tetrameric antibody complexes, and biotinylated antibodies.

The antibodies of the invention may be biotinylated and indirectly conjugated to a matrix which is labelled with (strept) avidin. For example, biotinylated antibodies contained in the antibody composition of the invention may be used in combination with magnetic iron-dextran particles that are covalently labelled with (strept) avidin (Miltenyi, S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35–44, at pages 36 to 39, and Ziolo et al. Science (1994) 257:219 which are incorporated herein by reference. Colloidal particles of dextran-iron complex are preferably used in the process of the invention. (See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference).

FIG. 1 is a schematic representation of magnetic cell labeling using tetrameric antibody complexes and colloidal dextran iron.

In accordance with the magnetic separation method, the sample containing the mesenchymal progenitor cells to be recovered, is reacted with the above described antibody reagents, preferably tetrameric antibody complexes, so that the antibody reagents bind to the non-mesenchymal progenitor cells present in the sample to form cell conjugates of the targeted non-mesenchymal progenitor cells and the antibody reagents. The reaction conditions are selected to provide the desired level of binding of the targeted non-mesenchymal progenitor cells and the antibody reagents. Preferably the sample is incubated with the antibody reagents for a period of 5 to 60 minutes at either 4° or ambient room temperature. The concentration of the antibody reagents is selected depending on the estimated concentration of the targeted cells in the sample. Generally, the concentration is between about 0.1 to 50 $\mu$g/ml of sample. The magnetic particles are then added and the mixture is incubated for a period of about 5 minutes to 30 minutes at the selected temperature. The sample is then ready to be separated over a magnetic filter device. Preferably, the magnetic separation procedure is carried out using the magnetic filter and methods described in U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a dipole magnet with a gap varying from 0.3 to 3.0 inches bore and having a magnetic field of 0.5–2 Tesla. The magnetically labelled cell conjugates are retained in the high gradient magnetic column and the materials which are not magnetically labelled flow through the column after washing with a buffer.

The preparation containing non-magnetically labelled cells may be analyzed using procedures such as flow cytometry.

In another embodiment, the mesenchymal progenitor enrichment composition may be used in an immunorosetting method wherein the cells to be depleted are rosetted with red blood cells or erythrocytes. In such an embodiment, each of the antibodies in the mesenchymal progenitor enrichment composition are linked to an antibody that binds to erythrocytes. FIG. 2 is a schematic representation of a rosette of erythrocytes formed around an unwanted nucleated cell using tetrameric antibody complexes.

Accordingly, the present invention provides a negative selection method for enriching and recovering mesenchymal progenitor cells in a sample containing the mesenchymal progenitor cells, erythrocytes and undesired cells comprising: (i) contacting the sample with an antibody composition comprising (1) antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig linked to (ii) at least one antibody that binds to the erythrocytes, under conditions to allow immunorosettes of the undesired cells and the erythrocytes to form; and (2) separating the immunorosettes from the remainder of the sample to obtain a sample enriched in mesenchymal progenitor cells.

The immunorosettes between the erythrocytes and the unwanted cells formed in step (1) can be separated from the desired cells using a variety of techniques. In one embodiment, the sample, containing the immunorosettes, is layered over a buoyant density solution (such as Ficoll-Hypaque) and centrifuged. The immunorosettes pellet and the desired cells remain at the interface between the buoyant density solution and the sample. The desired cells are then removed from the interface for further use. In another embodiment, the sample containing the immunorosettes obtained in step (1) is mixed with a sedimentation reagent (such as hydroxyethyl starch, gelatin or methyl cellulose) and the rosettes are permitted to sediment. The desired cells remain in suspension and are removed for further use. In a further embodiment, the sample containing the immunorosettes obtained in step (1) is allowed to sediment with or without the aid of centrifugation or Counter Flow Elutriation. The desired cells remain in suspension and are removed for further use.

The method of the invention may be used in the processing of biological samples that contain erythrocytes including blood (in particular, cord blood and whole blood) bone marrow, fetal liver, buffy coat suspensions, pleural and peritoneal effusions and suspensions of thymocytes and splenocytes. Surprisingly, the inventors have found that the method can be used to remove cells directly from whole blood or whole bone marrow without prior processing. This offers a significant advantage of the method of the invention over the prior art methods. In particular, the erythrocytes do not have to be removed, labelled and added back to the sample.

The following non-limiting examples are illustrative of the present invention:

EXAMPLES

Materials and Methods

Method of Culturing CFU-F

Human bone marrow samples are depleted of red blood cells using, for example, an ammonium chloride buffer. Alternatively, a mononuclear cell fraction can be prepared by density gradient separation using ficoll hypaque (Pharmacia). The cells are washed with phosphate buffered saline (PBS) containing 2% fetal bovine serum (FBS) and resuspended in MesenCult™ medium-a modified McCoy's based medium containing screened batches of FBS, selected for their ability to support CFU-F. The bone marrow cells are counted and diluted to give a final cell concentration of $2 \times 10^6$ cells per ml (stock solution) in MesenCult™ medium. Volumes of 1.0 ml, 0.5 ml and 0.25 ml of the cell stock solution are dispensed into separate 100 mm tissue culture treated dishes or 25 cc flasks. MesenCult™ medium is added to a final volume of 10 mls thereby yielding final cell concentrations of $2 \times 10^6$ cells, $1 \times 10^6$ cells and $0.5 \times 10^6$ per culture dish or flask. (These concentrations will ensure that the resulting numbers of colonies can be scored, as there are differences in the proliferative potential of CFU-F from various bone marrow samples). The cultures are placed into a 37° C. humidified incubator containing 95% $CO_2$, 95% air for 14 days. Maximum colony size and numbers are typically seen at this time. The colonies range from 1–8 mm and are easily identified using an inverted microscope (20–25× total magnification). Alternatively, the colonies may be scored macroscopically following staining.

Method of Staining CFU-F

The media is removed form the tissue culture dishes or flasks which are then washed twice with PBS. The cells are fixed with methanol (5 minutes room temperature) and stained with Wright Giemsa (5 minutes at room temperature). The culture dishes are then rinsed with distilled water.

Method of Preparing Tetrameric Antibody Complexes

In order to prepare a tetrameric antibody complex for use in an immunorosetting method of the present invention, the following protocol may be used: (a) take 1 mg of antibody specific for cells to be rosetted; (b) add 3 mg anti-Glycophorin A antibody (against red blood cells); mix well (c) then add 2.72 mg of the P9 $F(ab')_2$ antibody fragment. Incubate overnight at 37° C. The P9 antibody binds the Fc portion of the antibodies added in steps (a) and (b) resulting in a tetrameric antibody complex. For more information on the preparation of tetramers see U.S. Pat. No. 4,868,109 to Lansdorp, which is incorporated herein by reference. Tetrameric antibody complexes incorporating different antibodies to antigens expressed on the cells you wish to remove are prepared separately and then mixed.

The antibody compositions are made by combining various tetrameric antibody complexes depending on which cells one wishes to deplete. The concentration of the various tetrameric antibody complexes varies: antibodies to antigens expressed on the cells to be depleted are generally at 10–30 µg/mL in tetrameric complexes. The composition is then diluted 1/10 into the cells so the final concentrations of each anti nucleated cell antibody in the cell suspensions is 1.0–3.0 µg/mL.

Example 1

Method of Enriching CFU-F Using Immunorosetting

The frequency of CFU-F in normal bone marrow donors is very low (approximately 1:100,000). The ability to enrich for this cell type has been hampered by the fact that the precursor cell has no known distinctive antigenic determinants. (Certain antibodies have been generated against antigenic determinants for MSC but these are only found following the culturing of the cells). The approach to enrich CFU-F has involved the depletion of a certain cell population and quantitation of the CFU-F frequency.

Combinations of bifunctional tetrameric antibody complexes recognizing glycophorin A and different cell surface antigens were added to 2.0 mL bone marrow samples. Rosettes form between the erythrocytes (expressing glycophorin A) and nucleated cells expressing the specified cell surface antigens. Following a 20 minute incubation, the marrow was diluted with 4.0 mls of PBS containing 2% FBS and 1 mM EDTA and layered onto 6.0 mls of ficoll (Pharmacia). The cells were separated by density gradient centrifugation for 25 mins, 1200 rpm (break off). Rosetted cells settle in the pellet. Cells at the interface were removed carefully, washed in PBS+2% FBS+1 mM EDTA to remove any residual ficoll. The cells were resuspended in a known volume of MesenCult™.

The frequency of CFU-F was determined as described above and the fold enrichment calculated based on the following equation:

$$\frac{\text{frequency of CFU-F in ficoll}}{\text{frequency of CFU-F following enrichment procedure}}$$

The percent recovery of CFU-F were calculated based on the following equation:

$$\frac{\text{total number of CFU-F following enrichment of a 2 ml sample of bone marrow}}{\text{total number of CFU-F following ficoll of a 2 ml sample of bone marrow}} \times 100$$

Example 2

Comparison with Anti-CD45 Depletion

Mesenchymal Progenitor cells were enriched using the method described in Example 1. Two cocktails of tetrameric antibody complexes were prepared. One cocktail contained bifunctional tetrameric antibody complexes recognizing glycophorin A and CD45. The other cocktail contained bifunctional tetrameric antibody complexes recognizing glycophorin A and the following antigens; CD3, CD19 and CD66b. The results, shown in Table 2, demonstrate that depletion with anti-CD45 recovers less than 10% of the mesenchymal progenitors whereas the method of the invention (cocktail without anti-CD45) recovers essentially all of the mesenchymal progenitors. The cocktail without anti-CD45 also offers superior enrichment of mesenchymal progenitors.

Example 3

Negative Selection of Mesenchymal Progenitors with Lymphoid and Myeloid Specific Antibodies Mesenchymal Progenitor cells were enriched using the method described in Example 1. Two cocktails of tetrameric antibody complexes were prepared. One cocktail contained bifunctional tetrameric antibody complexes recognizing glycophorin A and CD2. The other cocktail contained bifunctional tetrameric antibody complexes recognizing glycophorin A and the following antigens: CD3 and CD66b. The results, shown in Table 3, demonstrate that depletion with anti-CD2 alone only offers two fold enrichment of mesenchymal progenitors. Adding anti-CD3 and a myeloid antibody, anti-CD66b improves the enrichment of mesenchymal progenitors to as much as 4.5 fold.

Example 4

Negative Selection of Mesenchymal Progenitors Using Anti-CD3, CD19 and CD66b Mesenchymal Progenitor cells were enriched using the method described in Example 1. Cocktails were prepared with combinations of tetrameric antibody complexes recognizing two or three different antigen expressed on nucleated cells. Cocktails contained bifunctional tetrameric antibody complexes recognizing glycophorin A and two other antigens (CD2 and CD19 or CD3 and CD66b) or three other antigens (CD3, CD19, and CD66b). The results, shown in Table 4, demonstrate that negative selection with the antibody combination of anti-CD3, CD19 and CD66b was superior to selection with only two antibodies to nucleated cells.

Example 5

Addition of Anti-CD14 to the Mesenchymal Progenitor Enrichment Cocktail

Mesenchymal Progenitor cells were enriched using the method described in Example 1. Two cocktails of tetrameric antibody complexes were prepared. One cocktail contained bifunctional tetrameric antibody complexes recognizing glycophorin A and three antigens expressed on nucleated cells (CD3, CD19, and CD66b). The other cocktail contained bifunctional tetrameric antibody complexes recognizing glycophorin A and four antigens expressed on nucleated cells (CD3, CD19, CD66b, and CD14). The results, shown in Table 5, demonstrate that adding anti-CD14 to the three antibody cocktail of anti-CD3, CD19 and CD66b doubled the fold enrichment of mesenchymal progenitors.

Example 6

Combinations of Anti-myeloid Antibodies

Mesenchymal Progenitor cells were enriched using the method described in Example 1. The anti-CD14 antibody in the cocktail described in Example 5 was substituted with anti-CD33 or anti-CD38. The results, shown in Table 6, demonstrate that substituting anti-CD14 with either CD33 or CD38 has little effect on the fold enrichment of mesenchymal progenitors. However, the results in Table 7 show that leaving in anti-CD14 and adding both anti-CD36 and CD38 improves the fold enrichment of mesenchymal progenitors from 8 to 10 fold. The results, shown in Table 6 and 7, suggest that anti-CD36 may remove a portion of the mesenchymal progenitors.

Example 7

Addition of Anti-CD34 to the Mesenchymal Progenitor Enrichment Cocktail

Mesenchymal Progenitor cells were enriched using the method described in Example 1. Two cocktails of tetrameric antibody complexes were prepared. One cocktail contained bifunctional tetrameric antibody complexes recognizing glycophorin A and five antigens expressed on nucleated cells (CD3, CD19, CD14, CD38 and CD66b). The other cocktail contained bifunctional tetrameric antibody complexes recognizing glycophorin A and six antigens expressed on nucleated cells (CD3, CD19, CD14, CD38, CD66b and CD34). The results, shown in Table 8, demonstrate that adding anti-CD34 to the five antibody cocktail of anti-CD3, CD19, CD14, CD38 and CD66b increased the fold enrichment of mesenchymal progenitors.

While what is shown and described herein constitutes various preferred embodiments of the subject invention, it will be understood that various changes can be made to such embodiments without departing from the subject invention, the scope of which is defined in the appended claims.

TABLE 1

Antibodies used in Cell Separation

| Antigen | Antibody | Source |
|---|---|---|
| CCR5 | BLR-7 | R&D, Minneapolis, MN |
| CD2 | 6F10.3 | IMMUNOTECH, Marseille, France |
|  | MT910 | Dako, Carpinteria, CA |
| CD3 | UCHT1 | IMMUNOTECH, Marseille, France |
|  | SK7 | Becton Dickinson Immunocytometry, Mountain View, Calif. |
| CD4 | 13B8.2 | Becton Dickinson Immunocytometry, Mountain View, Calif. |
| CD5 | UCHT2 | Serotec, Raleigh, NC |
| CD8 | B911 | Becton Dickinson Immunocytometry, Mountain View, Calif. |
|  | OKT3 | BioDesigns |
| CD10 | ALB1 | IMMUNOTECH, Marseille, France |
| CD11b | ICRF44 | Pharmingen, San Diego, CA |
| CD14 | MEM 15 | Exbio, Praha, Czech Republic |
|  | MEM 18 |  |
| CD15 | DU-HL60-3 | Sigma, St. Louis, MO |
| CD16 | MEM 154 | Exbio, Praha, Czech Republic |
|  | 3G8 | IMMUNOTECH, Marseille, France |
|  | NKP15 | Becton Dickinson Immunocytometry, Mountain View, Calif. |
| CD19 | J4.119 | IMMUNOTECH, Marseille, France |
|  | 4G7 | Becton Dickinson Immunocytometry, Mountain View, Calif. |
|  | HD37 | Dako, Carpinteria, CA |
| CD20 | MEM97 | Exbio, Praha, Czech Republic |
|  | L27 | Becton Dickinson Immunocytometry, Mountain View, Calif. |
| CD21 | B-Ly4 | Pharmingen, San Diego, CA |
| CD22 | HIB22 | Pharmingen, San Diego, CA |
| CD24 | 32D12 | Dr. Steinar Funderud, Institute for Cancer Research, Dept. of Immunology, Oslo, Norway |
|  | ALB9 | IMMUNOTECH, Marseille, France |
| CD25 | 3G10 | Caltaq, Burlingame, CA |
| CD27 | 1A4CD27 | IMMUNOTECH, Marseille, France |
| CD29 | Lia1.2 | IMMUNOTECH, Marseille, France |
| CD33 | D3HL60.251 | IMMUNOTECH, Marseille, France |
| CD34 | 581 | IMMUNOTECH, Marseille, France |
| CD36 | FA6.152 | IMMUNOTECH, Marseille, France |
|  | IVC7 | CLB, Central Laboratory of the Netherlands, Red Cross Blood Transfusion Service |
| CD38 | T16 | IMMUNOTECH, Marseille, France |
| CD41 | PI1.64 | Kaplan, 5th International Workshop on Human Leukocyte Differentiation Antigens |
|  | SZ22 | IMMUNOTECH, Marseille, France |
| CD42a | Bebl | Becton Dickinson Immunocytometry, Mountain View, Calif. |
| CD45 | J33 | IMMUNOTECH, Marseille, France |
|  | MEM28 | Exbio, Praha, Czech Republic |
| CD45RA | 8D2.2 | Craig et al. 1994, StemCell Technologies, Vancouver, Canada |
|  | L48 | Becton Dickinson Immunocytometry, Mountain View, Calif. |
| CD45RO | UCHL1 | Dako, Carpinteria, CA |
| CD56 | T199 | IMMUNOTECH, Marseille, France |
|  | MY31 | Becton Dickinson Immunocytometry, Mountain View, Calif. |
| CD66e | CLB/gran10 | CLB, Central Laboratory of the Netherlands, Red Cross Blood Transfusion Service |
| CD66b | B13.9 | CLB, Central Laboratory of the Netherlands, Red Cross Blood Transfusion Service |
|  | 80H3 | IMMUNOTECH, Marseille, France |
| CD69 | L78 | BD Biosciences, San Jose, CA |
| CD71 | My29 | Zymed Laboratories, San Francisco, CA |
| CD124 | S456C9 | IMMUNOTECH, Marseille, France |
| HLADR | IMMU357.12 | IMMUNOTECH, Marseille, France |
| IgA1 | NiF2 | IMMUNOTECH, Marseille, France |
| IgE | G7-18 | Pharmingen, San Diego, CA |
| IgG | 8A4 | IMMUNOTECH, Marseille, France |
| TCRαβ | WT31 | BD Biosciences, San Jose, CA |
| TCR γδ | Immu510 | IMMUNOTECH, Marseille, France |

TABLE 2

Comparison with Anti-CD45 Depletion

| Sample | Antibody Cocktails | Frequency of CFU-F | Recovery of CFU-F | Fold enrichment over control* |
|---|---|---|---|---|
| 1 | CD45 + glycophorin A | 1:16,000 | 6% | 5.9× |
|  | CD3 + CD19 + CD66b + glycophorin A | 1:10,600 | 100% | 8.8× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 3

Negative Selection of Mesenchymal Progenitors with Lymphoid and Myeloid Specific Antibodies

| Sample | Antibody Cocktails | Frequency of CFU-F | Recovery of CFU-F | Fold enrichment over control* |
|---|---|---|---|---|
| 1 | CD2 | 1:39,500 | 80% | 2× |
|  | CD3 + CD66b | 1:30,300 | 66% | 2.5× |
| 2 | CD2 | 1:46,000 | 100% | 2× |
|  | CD3 + CD66b | 1:20,500 | 71% | 4.5× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 4

Negative Selection of Mesenchymal Progenitors Using Anti-CD3, CD19 and CD66b

| Sample | Antibody Cocktails | Frequency of CFU-F | Recovery of CFU-F | Fold enrichment over control* |
|---|---|---|---|---|
| 1 | CD2 + CD19 | 1:49,500 | 68% | 1.5× |
|  | CD3 + CD66b | 1:30,300 | 66% | 2.5× |
|  | CD3 + CD19 + CD66b | 1:12,400 | 61% | 6× |

TABLE 4-continued

Negative Selection of Mesenchymal Progenitors Using Anti-CD3, CD19 and CD66b

| Sample | Antibody Cocktails | Frequency of CFU-F | Recovery of CFU-F | Fold enrichment over control* |
|---|---|---|---|---|
| 2 | CD3 + CD66b | 1:20,500 | 71% | 4.5× |
|   | CD3 + CD19 + CD66b | 1:10,613 | 100% | 8.8× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 5

Addition of Anti-CD14 to the Mesenchymal Progenitor Enrichment Cocktail

| Sample | Antibody Cocktails | Frequency of CFU-F | Recovery of CFU-F | Fold enrichment over control* |
|---|---|---|---|---|
| 1 | CD3 + CD19 + CD66b | 1:24,700 | 68% | 4.1× |
|   | CD3 + CD19 + CD66b + CD14 | 1:12,400 | 68% | 8× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 6

Combinations of Anti-myeloid Antibodies Substitutions for Anti-CD14

| Sample | Antibody Cocktails | Frequency of CFU-F | Recovery of CFU-F | Fold enrichment over control* |
|---|---|---|---|---|
| 1 | CD3 + CD19 + CD66b | 1:24,700 | 68% | 4.1× |
|   | CD3 + CD19 + CD66b + CD14 | 1:12,400 | 68% | 8× |
|   | CD3 + CD19 + CD66b + CD33 | 1:14,300 | 48% | 7× |
|   | CD3 + CD19 + CD66b + CD38 | 1:12,800 | 45% | 8× |
|   | CD3 + CD19 + CD66b + CD36 | 1:28,600 | 12% | 3.5× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 7

Combinations of Anti-myeloid Antibodies Addition of Anti-CD38, CD33 and CD36

| Sample | Antibody Cocktails | Frequency of CFU-F | Recovery of CFU-F | Fold enrichment over control* |
|---|---|---|---|---|
| 1 | CD3 + CD19 + CD66b + CD14 | 1:12,400 | 68% | 8× |
|   | CD3 + CD19 + CD66b + CD14 + CD33 | 1:14,900 | 54% | 7× |
|   | CD3 + CD19 + CD66b + CD14 + CD36 + CD38 | 1:10,400 | 27% | 10× |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

TABLE 8

Additon of Anti-CD34 to the Mesenchymal Progenitor Enrichment Cocktail

| Sample | Antibody Cocktails | Frequency of CFU-F | Recovery of CFU-F | Fold enrichment over control |
|---|---|---|---|---|
| 1 | CD3 + C19 + CD66b + CD14 + CD38 | 1:10,100 | 40% | 11 |
|   | CD3 + C19 + CD66b + CD14 + CD38 + CD34 | 1:11,100 | 41% | 10 |
| 2 | CD3 + C19 + CD66b + CD14 + CD38 | 1:5,700 | 48% | 8.5 |
|   | CD3 + C19 + CD66b + CD14 + CD38 +CD34 | 1:4,800 | 50% | 10 |

*The fold enrichment over control is calculated as follows:

$$\frac{\text{frequency of CFU-F in a ficolled bone marrow sample (without the addition of antibodies)}}{\text{frequency of CFU-F in bone marrow sample to which various antibody cocktails have been added}}$$

Full Citations for References Referred to in the Specification

1. Dexter T M, Allen T D, Lajtha L G. Conditions controlling the proliferation of haemopoietic stem cells in vitro. J Cell Physiol 91: 335–344, 1977
2. Waller E K, Olweus J, Lund-Johansen F, Huang S, Nguyen M, Guo G-R and Terstappen L. The "common stem cell" hypothesis reevaluated: human fetal bone marrow contains separate populations of hematopoietic and stromal progenitors Blood 85: 2422–2435, 1995
3. Owen M E, Cave J, Joyner C J. Clonal analysis in vitro of osteogenic differentiation of marrow CFU-F. J Cell Sci 87: 731–738, 1987
4. Caplan A I and Bruder S P. Cell and molecular engineering of bone regeneration In "Principles of tissue engineering" eds R Lanza, R Langer and W Chick RG Landes Company 1997, pp 603–618

5. Thiede M A, Majumdar M K, Jaiswal N, Pittenger M, Mackay A, Aksentijevich I and Mosca J D. Mesenchymal stem cells: function in formation of bone marrow stroma in vitro. Blood 92, suppl 1, 528 (abstract), 1998
6. Clarke E and McCann S R. Age dependent in vitro stromal growth. Bone Marrow Transplant 4: 596–597, 1989
7. Minguell J J and Martinez J. Growth patterns and function of bone marrow fibroblasts from normal and acute lymphoblastic leukemic patients. Exp Hematol 11: 522–526, 1983
8. Nagao T, Yamauchi K and Komatsuda M. Serial in vitro bone marrow fibroblast culture in human leukemia. Blood 61: 588–592, 1983
9. Reynolds M and McCann S R. A comparison between regimens containing chemotherapy alone (busulphan and cyclophosphamide) and chemotherapy (V RAPID) plus total body irradiation on marrow engraftment following allogeneic bone marrow transplantation. Eur J Haematol 43: 314–320, 1989
10. Lazarus H M, Haynesworth S E, Gerson S L, Rosenthal N S and Caplan A I. Ex vivo expansion and subsequent infusion of human bone marrow-derived stromal progenitor cells (mesenchymal progenitor cells): implications for therapeutic use. Bone Marrow Transplant 16: 557–264, 1995
11. Pereira R F, O'Hara M D, Laptev A V, Halford K W, Pollard M D, Class R, Simon D, Livezey K, Prockpop D J. Marrow stromal cells as a source of progenitor cells for nonhematopoietic tissues in transgenic mice with a phenotype of osteogenesis imperfecta. Proc Natl Acad Sci (USA) 95: 1142–1147, 1998
12. Horwitz E M, Prockpop D J, Marini J C, Fitzpatrick L A, Gordon P, Koo W, Neel M, Orchard P and Brenner M. Bone marrow transplantation to correct the mesenchymal defect of children with osteogenesis imperfecta. Blood 92:, suppl 1, 249 (abstract), 1998
13. Bruder S P, Kurth A A, Shea M, Hayes W C, Jaiswai N and Kadiyala S. Bone regeneration by implantation of purified, culture-expanded human mesenchymal stem cells. J Orthop Res 16:155–162, 1998

We claim:

1. A negative selection process for enriching and recovering human mesenchymal progenitor cells in a sample containing human mesenchymal progenitor cells wherein said process comprises (1) reacting the sample with an antibody composition containing antibodies capable of binding to the antigens (a) CD2 and/or CD3 and/or CD5 and/or both CD4 and CD8; (b) CD66b and/or CD16 and/or OD11b and/or CD15; and (c) CD19 and/or CD20 and/or CD21 and/or CD22 and/or CD24 and/or Ig, under conditions so that conjugates are formed between the antibodies and cells in the sample containing the antigens (a) CD2 and/or CD3 and/or CD5 and/or both CD4 and CD8; (b) CD66b and/or CD16 and/or OD11b and/or CD15; and (c) CD19 and/or CD20 and/or CD21 and/or CD22 and/or CD24 and/or Ig, on their surfaces; (2) removing the conjugates; and (3) recovering a cell preparation which is enriched in human mesenchymal progenitor cells.

2. A process according to claim 1, wherein the antibodies in the antibody composition are monoclonal antibodies.

3. A process according to claim 2, wherein the antibodies in the antibody composition are labelled with a marker or they are conjugated to a matrix.

4. A process according to claim 3, wherein the antibodies in the antibody composition are labelled with biotin or a fluorochrome.

5. A process according to claim 3, wherein the matrix is magnetic beads, a panning surface, dense particles for density centrifugation, an adsorption column, or an adsorption membrane.

6. A process according to claim 2, wherein each of the monoclonal antibodies in the antibody composition is incorporated in a tetrameric antibody complex which comprises a first monoclonal antibody of a first animal species from the antibody composition, and a second monoclonal antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

7. A negative selection method for enriching and recovering human mesenchymal progenitor cells in a sample containing the human mesenchymal progenitor cells and erythrocytes comprising: (1) contacting the sample with an antibody composition comprising (i) antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig, wherein each of the antibodies in the antibody composition is linked to (ii) at least one antibody that binds to the erythrocytes, under conditions to allow immunorosettes of cells that bind to the antibodies in the antibody composition and the erythrocytes to form; and (2) separating the immunorosettes from the remainder of the sample to obtain a sample enriched in human mesenchymal progenitor cells.

8. A negative selection method for enriching and recovering human mesenchymal progenitor cells in a sample containing the human mesenchymal progenitor cells and erythrocytes comprising: (1) contacting the sample with an antibody composition comprising (i) antibodies capable of binding to the antigens (a) CD3; (b) CD66b; (c) CD19; (d) CD14 and (e) CD33 or CD38, wherein each of the antibodies in the antibody composition is linked to (ii) at least one antibody that binds to the erythrocytes, under conditions to allow immunorosettes of cells that bind to the antibodies in the antibody composition and the erythrocytes to form; and (2) separating the immunorosettes from the remainder of the sample to obtain a sample enriched in human mesenchymal progenitor cells.

9. A negative selection process according to claim 1 wherein the antibody composition comprises antibodies specific for the antigens (a) CD3; (b) CD66b and (c) CD19.

10. A negative selection method according to claim 7 wherein the antibody that binds to the erythrocytes is anti-glycophorin A.

11. A negative selection method according to claim 8 wherein the antibody that binds to the erythrocytes is anti-glycophorin A.

12. A negative selection process for enriching and recovering human mesenchymal progenitor cells in a sample containing human mesenchymal progenitor cells wherein said process comprises (1) reacting the sample with an antibody composition containing antibodies capable of binding to the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig; (d) CD14 and (e) CD33 and/or CD38, under conditions so that conjugates are formed between the antibodies and cells in the sample containing the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig; (d) CD14 and (e) CD33 and/or CD38, on their surfaces; (2) removing the conjugates; and (3) recovering a cell preparation which is enriched in human mesenchymal progenitor cells.

13. A negative selection process according to claim 12 wherein the antibody composition comprises antibodies specific for the antigens (a) CD3; (b) CD66b; (c) CD19; (d) CD14 and (e) CD33 or CD38.

14. A negative selection process according to claim 12 wherein the antibody composition comprises antibodies specific for the antigens (a) CD3; (b) CD66b; (c) CD19; (d) CD14 and (e) CD38.

15. A negative selection process for enriching and recovering human mesenchymal progenitor cells in a sample containing human mesenchymal progenitor cells wherein said process comprises (1) reacting the sample with an antibody composition containing antibodies capable of binding to the antigens (a) CD2 and/or CD3 and/or CD5 and/or both CD4 and CO8; (b) CD66b and/or CD16 b and/or CD11b and/or CD15; and (c) CD19 and/or CD20 and/or CD21 and/or CD22 and/or CD24 and/or Ig; (d) CD14; (e) CD33 and/or CD38; and (f) CD56, under conditions so that conjugates are formed between the antibodies and cells in the sample containing the antigens (a) CD2 and/or CD3 and/or CD5 and/or both CD4 and CD8; (b) CD66b and/or CD16 and/or CD11b and/or CD15; and (c) CD19 and/or CD20 and/or CD21 and/or CD22 and/or CD24 and/or Ig; (d) CD14; (e) CD33 and/or CD38; and (f) CD56, on their surfaces; (2) removing the conjugates; and (3) recovering a cell preparation which is enriched in human mesenchymal progenitor cells.

16. A negative selection process according to claim 15 wherein the antibody composition comprises antibodies specific for the antigens (a) CD3; (b) CD66b; (c) CD19; (d) CD14; (e) CD36; and (f) CD38.

17. A negative selection method for enriching and recovering human mesenchymal progenitor cells in a sample containing the human mesenchymal progenitor cells and erythrocytes comprising: (1) contacting the sample with an antibody composition comprising (i) antibodies capable of binding to the antigens (a) CD3; (b) CD66b; (c) CD19; (d) CD14; (e) CD36; and (f) CD38, wherein each of the antibodies in the antibody composition is linked to (ii) at least one antibody that binds to the erythrocytes, under conditions to allow immunorosettes of cells that bind to the antibodies in the antibody composition and the erythrocytes to form; and (2) separating the immunorosettes from the remainder of the sample to obtain a sample enriched in human mesenchymal progenitor cells.

18. A negative selection method according to claim 8 wherein the antibody composition comprises antibodies capable of binding to the antigens (a) CD3; (b) CD66b; (c) CD19; (d) CD14; and (e) CD38, wherein each of the antibodies in the antibody composition is linked to anti-glycophorin A.

* * * * *